United States Patent
Fischer et al.

[11] Patent Number: 6,153,788
[45] Date of Patent: Nov. 28, 2000

[54] PROCESS FOR PREPARING ESTERS OF ETHYLENICALLY UNSATURATED CARBOXYLIC ACIDS

[75] Inventors: Wolfgang Fischer, Meerbusch; Dieter Margotte; Jürgen Meixner, both of Krefeld, all of Germany

[73] Assignee: Bayer Aktiengesellschaft, Leverkusen, Germany

[21] Appl. No.: 09/131,026

[22] Filed: Aug. 7, 1998

[30] Foreign Application Priority Data

Aug. 26, 1997 [DE] Germany .................... 197 37 017

[51] Int. Cl.[7] ............... C07C 69/52; C07C 67/26
[52] U.S. Cl. ............. 560/224; 560/205; 560/209
[58] Field of Search .................. 560/205, 224, 560/209

[56] References Cited

U.S. PATENT DOCUMENTS

| | | | |
|---|---|---|---|
| 3,717,672 | 2/1973 | McGee | 260/485 R |
| 4,192,685 | 3/1980 | Horike et al. | 430/283.1 |
| 5,096,938 | 3/1992 | Beck et al. | 522/100 |
| 5,349,075 | 9/1994 | Van Den Berg et al. | 554/170 |
| 5,350,877 | 9/1994 | Ritter et al. | 560/224 |
| 5,648,518 | 7/1997 | Ritter et al. | 560/224 |
| 5,747,597 | 5/1998 | Fujita et al. | 525/312 |
| 5,840,823 | 11/1998 | Licht et al. | 528/73 |

FOREIGN PATENT DOCUMENTS

| | | |
|---|---|---|
| 054105 | 12/1984 | European Pat. Off. . |
| 127766 | 2/1986 | European Pat. Off. . |

*Primary Examiner*—Paul J. Killos
*Assistant Examiner*—Taylor V Oh
*Attorney, Agent, or Firm*—Joseph C. Gil; Thomas W. Roy

[57] ABSTRACT

The present invention relates to a process for preparing unsaturated esters by azeo-tropically esterifying a) monohydric or polyhydric alcohols or b) polyesters which contain at least two hydroxyl groups per molecule and are the reaction product of polyhydric alcohols with mono- or dibasis, saturated or aromatically unsaturated carboxylic acids, with ethylenically unsaturated carboxylic acids in the presence of an acid catalyst and subsequently reacting the acid catalyst and any unesterified carboxylic acid groups with ethylenically unsaturated monoepoxy compounds.

20 Claims, No Drawings

PROCESS FOR PREPARING ESTERS OF ETHYLENICALLY UNSATURATED CARBOXYLIC ACIDS

BACKGROUND OF THE INVENTION

1. Field of the Invention

The present invention relates to a process for producing esters by the acid-catalyzed azeotropic esterification of a hydroxy component and an ethylenically unsaturated carboxylic acid followed by the reaction of any residual acid with an ethylenically unsaturated mono-epoxy compound.

2. Description of the Prior Art

Esters of (meth)acrylic acid are employed, as reactive thinners, for example, in coating technology as well as in sealant compositions. These esters are (meth)acrylic acid esters which are based on mono- or polyhydric alcohols. The (meth)acrylic acid esters are generally produced by the azeotropic esterification of (meth)acrylic acid with mono- or polyhydric alcohols in an inert solvent using acidic catalysts, in the presence of stabilizers and while passing air through the reaction mixture. After esterification, the inert solvent is removed by distillation. The resulting reactive thinners are used in combination with unsaturated lacquer resins, and occasionally also in combination with saturated lacquer resins, to obtain viscosities which are suitable for application. Curing of the resulting compositions can be effected by peroxide accelerator systems (conventional curing), by UV radiation using photoinitiators, or directly by using an electron beam.

These esters are also used in the form of polyether acrylates. This class of compounds is produced analogously to the reactive thinners, by the azeotropic esterification of (meth) acrylic acid with polyether alcohols of higher functionality. Their area of application is mainly as coating compositions curable by UV radiation or electron beam. Polyether acrylates can be combined with unsaturated lacquer resins, reactive thinners or inert solvents.

A further area of application is their use in the form of polyester acrylate resins. For the production of these so-called polyester acrylate resins, pre-condensates (polyester polyols) are produced from polyhydric alcohols and mono- or dibasic, saturated or aromatically unsaturated carboxylic acids by condensation in the melt. These pre-condensates must contain at least two hydroxyl groups per molecule, and are then reacted, analogously to the formation of the reactive thinners or polyether acrylates, by the acid-catalyzed azeotropic esterification with (meth)acrylic acid. Polyester acrylates are also predominantly cured by high-energy radiation and can be employed in combination with inert solvents or reactive thinners.

The (meth)acrylic acid esters can also be used as precursors for the production of other unsaturated resins, such as urethane acrylates or amine-modified polyether acrylates, for example.

During the production of (meth)acrylic acid esters by the previously discussed known process, a residual acid number of up to 20 (mg KOH/g resin) remains in most cases. However, this residual acid number imparts corrosive properties to the products, which can result in the formation of rust in containers, for example, which leads to contamination of the product and the de-stabilization of the product by metal ions. Residues of (meth)acrylic acid are also discernible by their odor and occasionally because they irritate the skin during handling operations. Accordingly, there have been many attempts to remove residual acids from the resins produced.

During the production of (meth)acrylic acid esters, the batch is washed with water or optionally with dilute caustic soda after azeotropic esterification to remove acid catalysts and possibly other acids. A residual acid number of up to 5 (mg KOH/g resin) remains in most cases, however. Also, emulsions which are difficult to separate can be formed.

Attempts have also been made to solve this problem by adding dissolved lime after the production of the (meth) acrylic acid ester, and removing the resulting insoluble calcium salt by filtration (e.g. U.S. Pat. No. 3,717,672). However, oily precipitates, which can only be filtered with difficulty, are often formed.

In addition, methods of producing (meth)acrylic acid esters are known in which after neutralization of the esterification catalyst the residual (meth)acrylic acid is reacted with an epoxy compound (e.g. EP-A 127 766, EP-A 54 105). Depending upon the type and amount of epoxide used, the viscosity of the final product also changes to a varying extent. Also, the neutralization products cannot be polymerized, i.e. they remain as constituents which cannot be chemically incorporated into the resulting polymer. This results in unwanted film properties during subsequent curing, e.g., low hardness or extractability.

It is an object of the present invention to produce (meth) acrylic acid esters such that the final product has a reduced acid number, without disadvantageously affecting the properties of polymerizable mixtures produced therewith, such as color, viscosity or reactivity, and without disadvantageously affecting the properties of lacquer films produced therefrom, such as hardness or extractability.

This object has been achieved in accordance with the present invention by reacting the acid catalyst and the residual (meth)acrylic acid with an ethylenically unsaturated monoepoxy compound after the production of the desired (meth)acrylic acid ester. This results in a significant decrease in the acid number to a value of less than 1 mg KOH/g resin. In addition, the resulting binder composition exclusively contains reaction products which are polymerizable and, thus, can be chemically incorporated into the final product.

SUMMARY OF THE INVENTION

The present invention relates to a process for preparing unsaturated esters by azeo-tropically esterifying a) monohydric or polyhydric alcohols or b) polyesters which contain at least two hydroxyl groups per molecule and are the reaction product of polyhydric alcohols with mono- or dibasic, saturated or aromatically unsaturated carboxylic acids, with ethylenically unsaturated carboxylic acids in the presence of an acid catalyst and subsequently reacting the acid catalyst and any unesterified carboxylic acid groups with ethylenically unsaturated monoepoxy compounds.

DETAILED DESCRIPTION OF THE INVENTION

Examples of suitable ethylenically unsaturated acids for use in the process according to the invention include acrylic acid, methacrylic acid and mixtures thereof.

Mono- or polyhydric, saturated, aliphatic or cycloaliphatic alcohols, which optionally contain ether groups, can be used as the alcohols for the process according to the invention. These alcohols have molecular weights of 32 to about 800. Examples of these alcohols include methanol, ethanol, the isomeric propanols, butanols and hexanols, cetyl alcohol, stearyl alcohol, ethylene glycol, propylene glycol, 1,4-butanediol, 1,5-pentanediol, neopentyl glycol, 1,6-hexanediol, glycerol, trimethylol-ethane, trimethylolpropane, pentaerythritol, 2-ethylhexanol, cyclohexanol and di-methylolcyclohexane. Other examples of these alcohols include alkoxylation products of the preceding alcohols with 1 to 5 moles ethylene oxide and/or propylene oxide per hydroxyl equivalent. The preceding polyhydric alcohols are suitable for preparing the ester precursors. Examples of suitable saturated or aromatically unsaturated carboxylic acids include monocarboxylic acids dicarboxylic acids such as succinic acid, glutaric acid, adipic acid, phthalic acid, isophthalic acid, terephthalic acid, substituted phthalic acids and the corresponding acid anhydrides also.

Inorganic or organic acids are used as acidic esterification catalysts in an amount of 0.1 to 3% by weight, based on the weight of the reaction components to be esterified. Examples of esterification catalysts include sulphuric acid, phosphoric acid, pyro-phosphoric acid, p-toluenesulphonic acid, styrene-divinylbenzene-sulphonic acid, chlorosulphonic acid and chloroformic acid. Preferred are sulphuric acid and p-tolu-enesulphonic acid.

The process according to the invention is conducted in a solvent which is immiscible with water and which can be distilled with water in the sense of a steam distillation operation. Suitable solvents are those which do not react with the reactants or change in the presence of the acid catalysts, such as hydrocarbons and halogen- or nitrogen-substitution products thereof, more preferably unsubstituted hydrocarbons.

Examples include aliphatic hydrocarbons such as hexane, heptane, octane and petroleum fractions having various boiling ranges; cycloaliphatic hydrocarbons such as cyclopentane, cyclohexane and methyl-cyclohexane; and aromatic hydrocarbons such as benzene, toluene and the isomeric xylenes. Preferred solvents are those which boil at 70 to 120° C. Cyclohexane, toluene and petroleum fractions which boil at 70 to 120° C. are especially preferred. Suitable solvents also include mixtures of the preceding solvents. The solvents are used in an amount of 10 to 100% by weight, preferably 15 to 50% by weight and more preferably 20 to 40% by weight, based on the weight of the reaction components to be esterified.

In accordance with one embodiment for producing the polyester acrylates, a solvent-free melt condensation of the alcohol components with the saturated or aromatically unsaturated carboxylic acids is formed before the reaction step in the solvent, and the resulting precursor is then azeotropically esterified with (meth)acrylic acid in the presence of the water immiscible solvent.

The process according to the invention is conducted in the presence of one or more polymerization inhibitors in an amount of 0.01 to 1% by weight, preferably 0.1 to 0.5% by weight, based on the weight of the (meth)acrylic acid and alcohol to be esterified. Suitable inhibitors are described, for example, in Houben-Weyl, Methoden der organischen Chemie, 4th Edition, Volume XIV/1, Georg Thieme Verlag, Stuttgart 1961, page 433 et seq. Examples include sodium dithionite, sodium hydrogen sulphide, sulphur, hydrazine, phenylhydrazine, hydrazobenzene, N-phenyl-β-naphthylamine, N-phenyl-ethanolamine, dinitrobenzene, picric acid, p-nitrosodimethyl-aniline, diphenylnitrosamine, tetramethyl-thiuram disulphide, 2-mercaptobenzthiazole, the sodium salt of dimethyl-dithiocarbamic acid, and phenols such as p-tert.-butyl-catechol, 2,5-di-tert.-amyl-hydroquinone, p-alkoxyphenols and di-tert.-butylhydroquinone.

In a preferred embodiment of the process according to the invention an oxygen-containing gas, preferably air or mixtures of oxygen and inert gases, is passed through the solvent-containing reaction mixture.

In accordance with the process according to the invention esterification of the (meth)acrylic acid is carried out at a temperature of 60 to 140° C., preferably 70 to 120° C., and more preferably at the boiling point of the solvent. During the reaction, solvent is continuously removed by distillation from the reaction mixture, separated from entrained water in a water separator outside the reaction vessel, and then recycled to the reaction mixture. The end of the reaction is reached when no more water of reaction is entrained from the reaction vessel.

After the esterification reaction is complete, the reaction of the ethylenically unsaturated epoxy compound is carried out, preferably after distilling off the water-immiscible solvent.

Examples of ethylenically unsaturated mono-epoxy compounds, which can be used according to the invention, include glycidyl acrylate (2,3-epoxypropyl acrylate), glycidyl methacrylate (2,3-epoxypropyl methacrylate) and the addition products of 1 mole of acrylic acid or methacrylic acid with bis-epoxy compounds, such as hexanediol bisglycidyl ether, bisphenol A-bis-glycidyl ether or hexahydrophthalic acid bisgilycidyl ester.

The epoxy compound according to the invention is used in an equivalent ratio of epoxy groups to acid groups of 1.2:1 to 2:1, preferably 1.6:1. The reaction is carried out at elevated temperature, preferably 80 to 120° C., more preferably 90 to 110° C.

The reaction of the ethylenically unsaturated monoepoxy compoun with the acid can optionally be conducted in the presence of catalysts.

Suitable catalysts include quarternary ammonium halides such as tetrabutylammonium bromide or iodide; triphenylphosphine; phosphonium salts such as ethyltriphenylphos-phonium iodide; and alkali halides such as potassium iodide. The reaction is continued until the acid number has fallen to a value of <1 (mg KOH/g substance).

The present invention also relates to the use of the (meth)acrylic acid esters obtained according to the invention as binders or reactive thinners in radiation-curing or conventionally-curing sealant and coating compositions.

EXAMPLES

Example 1

Production of an Acrylic Acid Ester From an Ether Polyol 310 g of a triol produced from trimethylolpropane and 4 moles ethylene oxide, 187.2 g of acrylic acid, 1.5% by weight of p-toluenesulphonic acid, 3000 ppm of p-methoxyphenol and 200 ppm of 2,5-di-tert.-butylhydroquinone were added to a reaction vessel and mixed with 160 g of isooctane with stirring. (The % by weight and the ppm's were based on the weight of the polyol and acrylic acid.) The batch was heated to the reflux temperature (about 100° C.) with continuous stirring, while air was passed through the batch (one vessel volume per hour) and while passing nitrogen over the batch (two vessel volumes per hour). The water of reaction which formed was separated, and the batch was maintained under reflux until an acid number of about 5 (mg KOH/g substance) was reached. Thereafter, the batch was cooled to 50° C. and the isooctane was distilled off under vacuum at 90° C. and 50 mbar pressure. The apparatus was aerated and cooled to 60° C. 8.52 g of glycidyl methacrylate were added at 60° C., and the batch was heated to 100° C. while passing air through it and nitrogen over it, and was held at 100° C. for 1 hour. Thereafter, the batch was cooled. The resulting acrylic acid ester was clear and had an acid number of <(mg KOH/g substance) and a viscosity of 150 to 200 mPa.s at 23° C.

Example 2

Production of a Polyester Acrylate 195.2 g of succionic anhydride, 215.9 g of terephthalic acid, 174.3 g of trimethylol-propane, 413.8 g of diethylene glycol and 99.5 g of a triol produced from tri-methylolpropane and 4 moles ethylene oxide were added to a reaction vessel and heated, while passing nitrogen over the batch (twice the vessel volume per hou), and with stirring above 80° C. The reaction vessel was heated from 160° C. to 230° C. so that the emerging gas/water stream did not exceed 105° C. (head temperature). The temperature was held at 230° C. until an acid number of <3 (mg KOH/g substance) was reached (about 5 hours). Then the batch was cooled to 40° C. and the apparatus was modified for azeo-tropic esterification (water trap). 240.3 g of cyclohexane, 351 g of acrylic acied, 1.5% by weight of p-toluenesulphonic acid, 3000 ppm of p-methoxy-phenol and 200 ppm of di-tert.-butylhydroquinone were added to the polyester precursor, while passing air (one vessel volume per hour) through the batch and while passing nitrogen (two vessel volumes per hour) over the batch. (The % by weight and the ppm's were based on the weight of the polyester precursor and acrylic acid.) The batch was heated to reflux with stirring (about 85 to 90° C.) and was maintained under vigorous reflux until an acid number of <4 (mg KOH/g substance) was reached. The apparatus was cooled to 40° C. and modified for distillation. A vacuum of about 50 mbar was applied and cyclohexane was distilled off at 50 mbar and 90° C. 27.7 g of glycidyl methacrylate were added at 60° C. and the batch was heated to 100° C. while passing air through it and nitrogen over it, and was held for 2 hours at this temperature. Thereafter, the batch was cooled. The resulting polyester acrylate was clear and had an acid number of <1 mg KOH/g substance) and a viscosity of about 7000 mnPa.s as 23° C.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing an unsaturated ester by azeo-tropically esterifying
    a) a monohydric or polyhydric alcohol or
    b) a polyester which contains at least two hydroxyl groups per molecule and is the reaction product of a polyhydric alcohol with a mono- or di-basic, saturated or aromatically unsaturated carboxylic acid,
with an ethylenically unsaturated carboxylic acid in the presence of an acid catalyst and subsequently reacting the acid catalyst and any unesterified carboxylic acid groups with an ethylenically unsaturated monoepoxy compound.

2. The process of claim 1 wherein said ethylenically unsaturated carboxylic acid comprises acrylic acid and/or methacrylic acid.

3. The process of claim 1 wherein said ethylenically unsaturated monoepoxide comprises glycidyl acrylate and/or glycidyl methacrylate.

4. The process of claim 2 wherein said ethylenically unsaturated monoepoxide comprises glycidyl acrylate and/or glycidyl methacrylate.

5. The process of claim 1 wherein said ethylenically unsaturated monoepoxide is the reaction product of 1 mole of a bisepoxide and 1 mole acrylic acid and/or methacrylic acid.

6. The process of claim 2 wherein said ethylenically unsaturated monoepoxide is the reaction product of 1 mole of a bisepoxide and 1 mole acrylic acid and/or methacrylic acid.

7. The process of claim 1 wherein 1.2 to 2.0 equivalents of epoxide are used per equivalent of residual acid.

8. The process of claim 2 wherein 1.2 to 2.0 equivalents of epoxide are used per equivalent of residual acid.

9. The process of claim 3 wherein 1.2 to 2.0 equivalents of epoxide are used per equivalent of residual acid.

10. The process of claim 4 wherein 1.2 to 2.0 equivalents of epoxide are used per equivalent of residual acid.

11. The process of claim 5 wherein 1.2 to 2.0 equivalents of epoxide are used per equivalent of residual acid.

12. The process of claim 6 wherein 1.2 to 2.0 equivalents of epoxide are used per equivalent of residual acid.

13. The process of claim 1 which comprises reacting the acid catalyst and any unesterified carboxylic acid groups with the ethylenically unsaturated monoepoxy compound at a temperature of 80 to 120° C.

14. A process for preparing an unsaturated ester by azeotropically esterifying
    a) a polyhydric alcohol or
    b) a polyester which contains at least two hydroxyl groups per molecule and is the reaction product of a polyhydric alcohol with a mono- or dibasic, saturated or aromatically unsaturated carboxylic acid, with an ethylenically unsaturated carboxylic acid in the presence of an acid catalyst and subsequently reacting the acid catalyst and any unesterified carboxylic acid groups with an ethylenically unsaturated monoepoxy compound.

15. The process of claim 14 wherein said ethylenically unsaturated carboxylic acid comprises acrylic acid and/or methacrylic acid.

16. The process of claim 14 wherein said ethylenically unsaturated monoepoxide comprises glycidyl acrylate and/or glycidyl methacrylate.

17. The process of claim 15 wherein said ethylenically unsaturated monoepoxide comprises glycidyl acrylate and/or glycidyl methacrylate.

18. The process of claim 14 wherein said ethylenically unsaturated monoepoxide is the reaction product of 1 mole of a bisepoxide and 1 mole acrylic acid and/or methacrylic acid.

19. The process of claim 15 wherein said ethylenically unsaturated monoepoxide is the reaction product of 1 mole of a bisepoxide and 1 mole acrylic acid and/or methacrylic acid.

20. The process of claim 14 wherein 1.2 to 2.0 equivalents of epoxide are used per equivalent of residual acid.

* * * * *